US006670325B2

(12) United States Patent
Lezdey et al.

(10) Patent No.: US 6,670,325 B2
(45) Date of Patent: Dec. 30, 2003

(54) TREATMENT OF OSTEOCARCINOMA WITH ALPHA-1—ANTITRYPSIN OR SECRETORY LEUCOCYTE PROTEASE INHIBITOR

(75) Inventors: John Lezdey, Indian Rocks Beach, FL (US); K. Anne Kronis, Tampa, FL (US); Darren Lezdey, Indian Rocks Beach, FL (US)

(73) Assignee: Alpha Med Pharmaceuticals Corp., Clearwater, FL (US)

( * ) Notice: Subject to any disclaimer, the term of this patent is extended or adjusted under 35 U.S.C. 154(b) by 0 days.

(21) Appl. No.: 10/034,265

(22) Filed: Oct. 19, 2001

(65) Prior Publication Data

US 2003/0077266 A1 Apr. 24, 2003

(51) Int. Cl.[7] ........................ A61K 38/17; A61K 38/55; A61K 38/57
(52) U.S. Cl. ........................................... 514/8
(58) Field of Search ............................................. 514/8

(56) References Cited

U.S. PATENT DOCUMENTS 5,492,889 A * 2/1996 Lezdey et al. ................. 514/8

FOREIGN PATENT DOCUMENTS

| DE | 19953732 A1 * | 5/2001 | ........... C07K/16/00 |
| WO | WO 0051624 A2 * | 9/2000 | ........... A61K/38/00 |

* cited by examiner

Primary Examiner—Jon P. Weber
(74) Attorney, Agent, or Firm—John Lezdey

(57) ABSTRACT

The present invention relates to the treatment of cancerous conditions in mammals by the administration to the site of disease compositions containing serine protease inhibitor. The cancerous conditions include osteocarcinomas, melanoma, Karopsi sarcoma and keratosis. The compositions are also useful to relieve the pain associated with the disease.

3 Claims, No Drawings

TREATMENT OF OSTEOCARCINOMA WITH ALPHA-1—ANTITRYPSIN OR SECRETORY LEUCOCYTE PROTEASE INHIBITOR

FIELD OF THE INVENTION

The present invention relates to the treatment of cancer and to the pain associated with cancer. The compositions utilized consist of protease inhibitors which prevent the proliferation of cancer cells and bind with the protease released by the cancer cells.

BACKGROUND OF THE INVENTION

It has been recognized by those in the medical field that the involvement in most cancers and their proliferation are:

1. Tumor necrosis factor alpha (TNF-α)
2. Matrix metalloproteases
3. Viruses

Viruses such as human papilloma viruses can lead to cancer, such as cervical cancer.

Matrix metalloproteases especially metallo-elastase have been found to be involved in lung cancer as well as skin cancer.

Tumor necrosis factor alpha has been found to be a cause of the proliferation of cells, especially renegade cells in the cell cycle.

Alpha$_1$-antitrypsin (α1-AT) belongs to serpin superfamily of serine protease inhibitor. It is a small glycoprotein which is mostly synthesized in the liver and has a molecular weight of 53,000 daltons. Human $_x$1-proteinase inhibitor is involved in the regulation of proteolysis, such as the coagulation pathway, fibrinolysis, tissue destruction by endogenous serine proteinases and inflammation.

U.S. Pat. No. 5,492,889 to Lezdey et al, which is herein incorporated by reference, discloses the treatment of mast cell tissues by the administration of alpha$_1$-antitrypsin alone or in combination with other serine protease inhibitors.

SUMMARY OF THE INVENTION

The present invention provides a method of treating of cancer with a protease inhibitor which is anti-tryptase and anti-inflammatory. More specifically, the treatment provides treatment of the tumor with a composition containing an effective amount of a serine protease inhibitor selected from the group consisting of alpha$_1$-antitrypsin, secretory leucocyte protease inhibitor (SLPI), alpha$_1$-antichymotrypsin, and mixtures thereof According to the invention, the cancers which can be treated are osteocarcinoma, cervical cancer, Karposi sarcoma, melanoma, histocytic tumors, malignant lymphomas, bladder cancer, breast cancer, and the like.

It is a general object of the invention to provide a composition and method for treating cancers and the symptoms thereof.

It is a further object of the invention to provide a composition for treating individuals having the symptoms of bone cancer.

It is another object of the invention to treat an individual wherein the cancer is caused as a result of human papilloma virus.

It is yet another object of the invention to treat skin cancer.

It is still a further object of the invention to provide a method and composition for treating cancers with serine protease inhibitors wherein there is a proliferation of cells resulting from the activity of TNF-α.

DESCRIPTION OF THE PREFERRED EMBODIMENTS

In accordance with one embodiment of the invention, there is provided a method for the treatment of individuals suffering from cancer or symptoms thereof by the administration of a serine protease inhibitor. The method consists of the administration of an effective therapeutic amount of a protease inhibitor selected from the group consisting of alpha$_1$-antitrypsin, secretory leucocyte protease inhibitor, alpha$_1$-antichymotrypsin, or mixtures thereof and analogs or derivatives thereof.

Accordingly, a composition containing at least about 10 mg of protease inhibitor in a suitable pharmaceutical vehicle is preferably injected at the site of the cancer. If metaastitis has taken place, then infusion into the patient is preferred together with injection.

Preferably, about 20 to 40 mg of the protease inhibitor in its natural, transgenic or recombinant form is dissolved in an aqueous medium, such as saline or buffer solution, and injected into the site of the cancer. The treatment provides immediate relief of pain since the kinins and kallikreins can be controlled. The patient can be treated daily until the cancers are reduced and under normal bodily control.

A cocktail of protease inhibitors is particularly effective which includes alpha$_1$-antichymotrypsin because it can control basophil infiltration.

Serine protease inhibitors have been found to play a major role on the direct inactivation of the mediators of inflammation so that the normal healing process can be accelerated without interference from the excess of material released at the site of inflammation. The almost immediate disappearance of pain indicates that there can be a control of the kinins as well.

The method also provides the oral or suppository administration of a protease inhibitor selected from the group consisting of alpha$_1$-antitrypsin, secretory leucocyte protease inhibitor, or mixtures thereof for use in maintenance and to prevent reoccurrence of the cancer if the immune system has been disrupted.

The drug can be administered in unit dosage form containing about 10 to 100 mg per day depending on the severity of the disease. The use of controlled release substances, for example, liposomes, diketopyperazine microparticles as disclosed by U.S. Pat. Nos. 5,620,708 and 5,503,852 which are herein incorporated by reference, and the delivery systems of U.S. Pat. No. 5,620,708 which is herein incorporated by reference.

It has been found that a complex of matrix metalloproteinase elastase and alpha2-macroglubulin promotes the proliferation of cancerous cells. It is believed that alpha$_1$-antitrypsin has a kinetic energy which will form a complex with the elastase matrix which is neutrophil elastase and/or metalloproteainase elastase so as to prevent the formation of the alpha2-macroglobulin-elastase complex. Also, SLPI and to a lesser degree alpha$_1$-antichymotrypsin will form a complex with elastase. Consequently, there is a reduction of the elastase, especially with alpha$_1$-antitrypsin.

Tumor necrosis factor alpha (TNF-α) has been reported as being involved in the proliferation of cells, especially deformed cells and cancerous cells. TNF-$_x$ is generally formed by the degradation of mast cells which occurs during viral or inflammatory attacks. Alpha$_1$-antitrypsin binds with IgE to prevent degradation of mast cells and also binds with TNF-α.

Alpha$_1$-antitrypsin and SLPI are anti-viral agents which can kill on contact human papilloma virus which causes cervical cancers.

Alpha$_1$-antitrypsin has been found by Lezdey et al to effectively treat the lesions of HPV and SLPI, kills on contact the HPV so that the proliferation is stopped and treatment of the abnormal cells can be effective.

Alpha2-macroglobulin by itself has no effect on cancer. However, the complex of alpha2-macroglobulin and elastase or matrix metalloproteainase elastase has been found to be used by cancer cells to break down and remodel tissue matrices during the process of metatastasis. Therefore, alpha$_1$-antitrypsin and/or SLPI can compete to bind with the elastase to prevent the formation of the alpha2-macroglobulin-elastase complex.

The protease inhibitors not only bind with the protease released by the cancer cells, but bind with the bradykinnins and kallikreins to alleviate pain. Alpha$_1$-antitrypsin prevents the degranulation of the mast cells so that the inflammation is further reduced to eliminate the pain associated with the disease.

Two likely proteases implicated in cell growth and division are the membrane-bound trypsin-like protease hepsin and a recently discovered putative tumor suppressor gene that also encodes a trypsin-like protease (Torres-Rasado et al Proc. Natl. Acad. Sci. USA 90, 7181–7185 (1993)). The proteases are elevated in regions of active cell proliferation in the developing mouse embryo. The protease inhibitors, especially alpha1-antitrypsin complexes with these trypsin-like proteases to suppress tumor growth.

The following example further illustrates the practice of this invention, but are not intended to be limiting thereof. It will be appreciated that the selection of actual amounts of specific protease inhibitor to be administered to any individual patient will fall within the discretion of the attending physician and will be prescribed in a manner commensurate with the appropriate risk:benfit ration for that particular patient. Appropriate dosages will depend on the patient's age, weight, sex, stage of disease and like factors uniquely within the purview of the attending physician.

EXAMPLE 1

A composition for installation into bladders of female patients with bladder cancer is prepared as follows.

| Ingredients | Amount |
| --- | --- |
| 2% saline solution | 40 ml |
| alpha$_1$-antitrypsin | 20 mg |

The composition can be instilled weekly in the bladder of individuals.

EXAMPLE 2

The drug in liposomes that can be administered orally in order to transgress to gastric barrier and prevent disintegration in the stomach is prepared as follows.

Following the procedure of U.S. Pat. No. 4,239,754, a lipid phase made up of the three components lecithin, cholesterol and dicetyl-phosphate in a molar ration of 7:2:1 is prepared with 2.6 g of lecithin, 4.4 g of cholesterol and 0.31 g of dicetyl-phosphate by dissolving in 50 ml of chloroform and the solution was evaporated. 0.5 of alpha$_1$-antitrypsin was dissolved in saline solution together with 0.1 g of superoxide dismutase and added to the phospholipids. The mixture is then subject to sonification for 10 seconds.

EXAMPLE 3

A patient suffering from keratosis on the legs was administered daily a 10% by weight of alpha$_1$-antitrypsin in AQUAPHOR®.

After one week of topical administration the keratosis completely disappeared.

EXAMPLE 4

A nine year old Labrador retriever was diagnosed with bone cancer (osteocarcinoma) of the hip joint which was increasing in size at the rate of 30% each month. Radiation therapy had no effect. The patient was in pain and had difficulty in walking. The prognosis was death in two months.

The patient was administered by injection 10 mg of alpha$_1$-antitrypsin twice a week at the site of the tumor. After one injection, the patient appeared free of pain and the walk improved. After two weeks of treatment the patient was running playfully. After one month of treatment, x-rays showed that the size of the tumor had started to decrease and the patient was active and pain-free.

In lieu of alpha$_1$-antitrypsin there can utilize SLPI or alpha-antichymotrypsin or a combination of the protease inhibitors.

What is claimed is:

1. A method for treating a patient suffering from osteocarcinoma which comprises administering to the site of the osteocarcinoma an effective amount of a protease inhibitor selected from the group consisting of alpha1-antitrypsin, secretory leucocyte protease inhibitor, and mixtures thereof in a suitable pharmaceutically acceptable carrier.

2. The method of claim 1 wherein the protease inhibitor is alpha1-antitrypsin.

3. The method of claim 1 wherein the protease inhibitor is secretory leucocyte protease inhibitor.

* * * * *